(12) United States Patent
Siegert et al.

(10) Patent No.: US 8,759,585 B2
(45) Date of Patent: Jun. 24, 2014

(54) TWO-STAGE PROCESS FOR COST-EFFECTIVE DEPOSITION OF HOMOGENEOUS CATALYSTS IN MDA SYNTHESIS

(75) Inventors: Markus Siegert, Heidelberg (DE);
Torsten Mattke, Freinsheim (DE);
Tilmann Steinmetz, Gruenstadt (DE);
Hans-Juergen Pallasch, Kallstadt (DE);
Filip Nevejans, St. Gillis-Waas (BE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/510,680

(22) PCT Filed: Dec. 13, 2010

(86) PCT No.: PCT/EP2010/069526
§ 371 (c)(1),
(2), (4) Date: May 18, 2012

(87) PCT Pub. No.: WO2011/080059
PCT Pub. Date: Jul. 7, 2011

(65) Prior Publication Data
US 2012/0232307 A1    Sep. 13, 2012

(30) Foreign Application Priority Data
Dec. 18, 2009 (EP) .................................... 09179900

(51) Int. Cl.
*C07C 211/00* (2006.01)
(52) U.S. Cl.
USPC .......................................................... 564/331
(58) Field of Classification Search
None
See application file for complete search history.

(56) References Cited

U.S. PATENT DOCUMENTS

| | | | |
|---|---|---|---|
| 5,449,818 A | 9/1995 | Biskup et al. | |
| 6,229,043 B1 * | 5/2001 | Scherzer et al. | 560/333 |
| 6,433,219 B1 | 8/2002 | Stroefer et al. | |
| 6,576,788 B1 | 6/2003 | Penzel et al. | |
| 2003/0045745 A1 | 3/2003 | Hagen et al. | |
| 2003/0176626 A1 | 9/2003 | Hagen et al. | |
| 2010/0105951 A1 | 4/2010 | Wloka et al. | |
| 2010/0280195 A1 | 11/2010 | Siegert et al. | |
| 2012/0083626 A1 | 4/2012 | Steinmetz et al. | |

FOREIGN PATENT DOCUMENTS

| | | |
|---|---|---|
| EP | 0 570 799 | 11/1993 |
| EP | 1 288 190 | 3/2003 |
| EP | 1 344 766 | 9/2003 |
| WO | 99 40059 | 8/1999 |
| WO | 99 54289 | 10/1999 |
| WO | 2008 083997 | 7/2008 |

OTHER PUBLICATIONS

Armarego, et al. Purification of Laboratory Chemicals 5$^{th}$ edition, 2003, front matter and chapter 1, 23 total pages.*
Schauerte, K., et al., "Isocyanate," Polyurethane, Kunststoffhandbuch, 3$^{rd}$ Edition, vol. 7, Ch. 3, pp. 76-86, (1993).
International Search Report Issued Jun. 6, 2011 in PCT/EP10/69526 Filed Dec. 13, 2010.

* cited by examiner

*Primary Examiner* — Clinton Brooks
(74) *Attorney, Agent, or Firm* — Oblon, Spivak, McClelland, Maier & Neustadt, L.L.P.

(57) ABSTRACT

The invention provides a process for preparing diphenylmethanediamine, comprising the steps of:
a) reacting aniline with formaldehyde in the presence of an acid,
b) neutralizing the predominant part of the acid with ammonia and/or aqueous ammonia solution,
c) separating the reaction mixture from step b) into an aqueous phase and an organic phase,
d) neutralizing the other part of the acid, present in the organic phase, with aqueous alkali metal hydroxide solution,
e) separating the reaction mixture from step d) into an aqueous phase and an organic phase,
f) treating the aqueous phase obtained in step c) or optionally the combined aqueous phases from steps c) and e) with at least one oxide or hydroxide of an alkaline earth metal,
g) removing the ammonia obtained in step f).

20 Claims, No Drawings

TWO-STAGE PROCESS FOR COST-EFFECTIVE DEPOSITION OF HOMOGENEOUS CATALYSTS IN MDA SYNTHESIS

The present invention relates to a process for preparing diphenylmethanediamine from aniline with formaldehyde in the presence of an acid, the acid being neutralized in two stages, first with ammonia and, in the second stage, with aqueous alkali metal hydroxide solution. The ammonia is recovered from the resultant aqueous phase by treatment with oxides and/or hydroxides of alkaline earth metals, and is available again for neutralization.

The preparation of diphenylmethanediamine (MDA) by reaction of aniline with formaldehyde in the presence of an acid is known and has been widely described. In practice, the diphenylmethanediamine thus prepared is always obtained as a mixture with more highly condensed polyphenylenepolymethylenepolyamines. Below, "MDA" refers to a mixture of bicyclic diphenylmethanediamine and more highly condensed polyphenylenepolymethylenepolyamines.

In the art, MDA is usually converted by reaction with phosgene into diphenylmethane diisocyanate (MDI), which is a frequently used basic product for polyurethane production. For certain applications, for instance as crosslinkers in plastics or coating materials, it is also possible for pure bicyclic MDA to be used.

In the art, MDA is prepared, as described, by reaction of aniline with formaldehyde in the presence of an acid. Hydrochloric acid is an acid typically employed. Processes of this kind are general knowledge and are described in, for example, Kunststoffhandbuch, volume 7, polyurethanes, Carl Hanser, Munich, Vienna, 3rd edition, 1993, pages 76 to 86, and also in a large number of patent applications, WO 99/40059 being an example. By varying the ratio of acid to aniline and of formaldehyde to aniline it is possible to adjust the proportion of the bicyclic product in the MDA in accordance with requirements.

A problem affecting the preparation of MDA is the neutralization of the acid catalyst employed.

Known from EP 1 288 190 A2 is the neutralization with a base, more particularly NaOH, of the reaction mixture obtained in the reaction of aniline with formaldehyde in the presence of an acid.

EP 1 344 766 A2 discloses a two-stage treatment of the resultant reaction mixture, in which, in the first step, the reaction mixture is neutralized with a base and, in the second step, the organic phase removed, which comprises the MDA, is treated with a base. Bases used are alkaline earth metal hydroxides and alkali metal hydroxides, more particularly sodium hydroxide.

WO 2008/083997 A1 describes a process for preparing MDA wherein the acid used as catalyst is neutralized by addition of ammonia rather than of alkali/alkaline earth metal oxides and/or hydroxides. The ammonium salt formed in this neutralization is recovered by reaction of an oxide or hydroxide of an alkaline earth metal.

The neutralization of the acid present in the reaction discharge from MDA preparation, using aqueous sodium hydroxide solution, gives two phases: an aqueous phase and an organic phase. The aqueous phase comprises the salt formed by the neutralization of the acid; the organic phase comprises the reaction products along with unreacted organic starting compounds. Depending on the proportion of aniline used to formaldehyde and also on the proportion of acid used to aniline, the densities of the aqueous phase and of the organic phase are different. The aqueous phase may be lighter or heavier than the organic phase; the densities of the two phases may also be the same. Different proportions of the starting compounds and of the acid catalyst used are typically necessary in order to obtain MDA having different properties such as, for example, composition, dimer content, and oligomer content, etc. For an industrial application, the phase separation ought to proceed quickly and virtually to completion, and this requires a sufficiently large density difference between the two phases. In order to ensure a sufficiently high density difference between the two phases, it is often necessary to take technical measures, examples being dilution of one of the phases or concentration by evaporation of components (aniline/water). This implies a relatively high level of technical cost and complexity.

Moreover, in the case of a plant which has been set up, the pipeline connections dictate which phase is supplied to a particular further-processing step on its removal. A change of phase in the wake of altered proportions of the reactants or of the acid used, therefore, would necessitate reconstruction or a plant construction that was more complex from the outset, such as, for example, shifting of the separation layer, and additional valves.

A further problem affecting MDA preparation is the incidence of unwanted byproducts, which when the MDA is processed further to MDI may lead to unwanted instances of coloration. In the synthesis of MDA from formaldehyde and aniline, N-aminobenzylanilines are among the products formed. These compounds undergo rearrangement under acidic conditions and at elevated temperature to form MDA. If the MDA is phosgenated to form MDI, increased levels of N-aminobenzylanilines result in the formation of carbamoyl chlorides, which in the phosgenation do not split into isocyanates with the consequence that the end product contains chlorine. Furthermore, further condensation with formaldehyde may result in dihydroquinazolines being formed from the N-aminobenzylanilines—the dihydroquinazolines are known to have an adverse effect on the color values of the MDI prepared from the MDA.

It was an object of the present invention to provide a process for preparing MDA wherein the two phases formed in the neutralization of the acid present in the reaction discharge from the MDA preparation, independently of the proportions of aniline, formaldehyde, and acid employed, have a sufficient density difference, and wherein always the same phase has the higher or lower density, respectively, thereby removing the need for technical measures to bring about a sufficiently large density difference, and allowing an existing plant to be operated independently of the proportions of reactants and of acid that are employed, without reconstruction work or additional internals.

This object has been achieved by the process below for preparing diphenylmethanediamine and more highly condensed polyphenylenepolymethylenepolyamines, comprising the steps of:
a) reacting aniline with formaldehyde in the presence of an acid,
b) neutralizing the predominant part of the acid with ammonia and/or aqueous ammonia solution,
c) separating the reaction mixture from step b) into an aqueous phase and an organic phase,
d) neutralizing the other part of the acid, present in the organic phase, with aqueous alkali metal hydroxide solution,
e) separating the reaction mixture from step d) into an aqueous phase and an organic phase, f) treating the aqueous phase obtained in step c) or optionally the combined aqueous phases from steps c) and e) with at least one oxide or hydroxide of an alkaline earth metal, g) removing the ammonia obtained in step f).

In the case of the use of ammonia as neutralizing agent, the organic phase is heavier than the aqueous phase, irrespective of the proportions of aniline to formaldehyde and of acid to aniline that are employed. Technical measures which are typically necessary for increasing the density difference between the aqueous phase and the organic phase in the neutralization of the acid catalyst employed can be dispensed with. Since, in the first neutralizing step (step b)), the predominant part of the acid has already been removed from the organic phase, the problems described above of the varying density differences no longer occur in the second neutralizing step with aqueous alkali metal hydroxide solution, since the amount of sodium chloride formed in the neutralization is relatively small. The change in the density of the aqueous sodium hydroxide solution used, owing to the absorption of the sodium chloride, is small, and its density remains much greater than that of the organic phase. The use of aqueous sodium hydroxide solution in the second stage of the neutralization ensures that the total acid catalyst employed is neutralized. The second neutralizing step with aqueous alkali metal hydroxide solution, moreover, has the advantage of removing not only ammonia left in the organic phase but also ammonium salts left therein, in the form of ammonia, by salt conversion.

MDA prepared in accordance with the process of the invention surprisingly shows better color values than MDA prepared in a process likewise with single-stage neutralization of ammonia, single-stage neutralization with aqueous sodium hydroxide solution, or two-stage neutralization with aqueous sodium hydroxide solution in both stages.

The process of the invention is notable, furthermore, for the cost-saving replacement of a large part of the sodium hydroxide typically used as neutralizing agent by the significantly more cost-effective alkaline earth metal oxides. This partial replacement takes place with mediation by ammonia, which is used as primary neutralizing agent and which is recovered by reaction with CaO, for example, and can be used again.

The preparation of the MDA in step a) takes place, as described above, by reaction of aniline with formaldehyde in the presence of acids as catalysts. Processes of this kind are general knowledge and are described in, for example, Kunststoffhandbuch, volume 7, polyurethanes, Carl Hanser, Munich, Vienna, 3rd edition, 1993, pages 76 to 86, and also in a large number of patent applications, WO 99/40059 being an example. As acid in step a) it is preferred to use a mineral acid, more particularly hydrochloric acid.

In place of or in a mixture with formaldehyde it also possible to use at least one formaldehyde donor compound. The formaldehyde is employed more particularly in the form of aqueous formalin solution, alcoholic formalin solution, methyl hemiacetal, methylenimine of a primary amine, or N,N'-methylenediamine of a primary or secondary amine, and also para-formaldehyde.

The process of the invention can be carried out continuously, semibatchwise or batchwise, preferably continuously or semibatchwise.

In the case of the continuous regime, the reactants are metered into a reactor, in the desired proportion to one another, and from this reactor an amount of reaction production is taken which is equal to the inflow. Examples of reactors employed include tube reactors. In the case of the batchwise or semibatchwise regime, the reactants are metered into a batch reactor, which is provided preferably with a stirrer and/or with a pumped circulation, and from which the reaction product, once full reaction has taken place, is removed and passed on for working-up.

The process of the invention is carried out typically with a molar ratio of aniline to formaldehyde of 20 to 1.5, preferably 10 to 1.6, more preferably from 2.5 to 1.8. The molar ratio of acid to aniline is preferably 0.04 to 0.5, more preferably 0.04 to 0.25. With these ratios, there is increased formation of the respective bicyclic products in the reaction mixture.

As acid it is preferred to use mineral acids such as hydrochloric acid, sulfuric acid, and phosphoric acid, and very preferably hydrochloric acid.

The reaction is carried out preferably at a temperature in the range between 0 and 200° C., preferably between 20 and 150° C., and more particularly between 40 and 120° C. It has emerged that the increasing of the temperature is accompanied by a rise in the portion of the 2,2' and 2,4' isomers in the reaction product.

The pressure during the reaction is 0.1-50, preferably 1-10, bar absolute.

In the case of the batchwise and semibatchwise implementation of the reaction, it is possible, after complete metering of the feedstocks, for the reaction mixture to be subjected to a so-called aging procedure. For this purpose, the reaction mixture is left in the reactor or is transferred to a different reactor, preferably a stirred reactor. The temperature of the reaction mixture in this case is preferably above 75° C., more particularly in a range between 110 and 150° C.

The preparation in step a) is followed by the neutralization of the predominant part of the acid in step b) of the reaction mixture. For this purpose, ammonia is added to the reaction mixture. This ammonia can be supplied to the reaction mixture in gaseous form and optionally saturated with water, as aqueous ammonia solution, or as a mixture of both phases. The ammonia is preferably added as an aqueous solution. The concentration of the ammonia in this case is preferably 14% to 60% by weight, measured at 3 bar and room temperature, more preferably 25% by weight. It is preferred for at least 60%, more preferably at least 70%, and more particularly at least 90% of the acid present in the reaction mixture to be neutralized by the ammonia added.

In accordance with the invention, the ammonia is added in 1 to 2 times the stoichiometric amount, based on the acid catalyst employed, preferably in 1 to 1.7 times the stoichiometric amount. The ammonia and/or the aqueous ammonia solution can be added in one step or in two or more successive steps. If the ammonia and/or the aqueous ammonia solution is added in two or more steps, it is also possible for the two phases produced in the operation to be separated before the next addition, with the organic phase in each case being admixed again with ammonia and/or with aqueous ammonia solution. Ammonia and aqueous ammonia solution may in this case also be used each in alternation in the individual steps.

The combining of the ammonia with the reaction mixture is typically accomplished in a suitable mixing apparatus such as a stirred tank, a tube, which is optionally provided with static mixing elements, or in other apparatus. The addition of basic ammonia produces neutralization of the predominant part of the acid present in the reaction mixture, and, as a result, causes the formation of two immiscible phases: a lighter aqueous phase and a heavier organic phase. Neutralization takes place at an average temperature of 40 to 120° C. under a pressure of 1 to 10 bar absolute.

The mixture from step b) is present, as described, in an organic phase and an aqueous phase. The two phases are separated from one another in step c) by being decanted, for example. In comparison to neutralization with aqueous sodium hydroxide solution, it has emerged, surprisingly, that the phase boundary is better formed when aqueous ammonia solution is used as the neutralizing agent. This means a reduction in the extent to which the downstream washing operation, in particular, is burdened with aqueous wash phase.

Following removal of the aqueous phase, which comprises the ammonium salt of the acid used as catalyst, the other part of the acid, that left in the organic phase, is neutralized in step d) with aqueous alkali metal hydroxide solution. For this purpose it is possible to use sodium hydroxide and potassium hydroxide, for example; sodium hydroxide is used with preference.

In accordance with the invention, the aqueous sodium hydroxide solution is added up to a maximum of a stoichiometric excess of 2, based on the acid originally employed as catalyst in the reaction mixture, preferably up to a maximum of a stoichiometric ratio of 1, more preferably of not more than 0.5.

In one preferred embodiment of the invention, in step d), the pH of the organic phase is adjusted to >8.5, preferably to >9, more preferably to a level of >9.5, and very preferably >11. In this way it is possible to ensure that the entirety of the acid present in the MDA-containing phase is neutralized, even in the typically very voluminous production plants for MDA.

The combining of the aqueous alkali metal hydroxide solution with the reaction mixture is accomplished typically in a suitable mixing apparatus such as a stirred tank, a tube, which is optionally provided with static mixing elements, or in other apparatus. The addition of the aqueous alkali metal hydroxide solution produces neutralization of the reaction mixture and so causes the formation of two immiscible phases: the aqueous phase and the organic phase. Neutralization takes place at an average temperature of 40 to 120° C. under a pressure of 1 to 10 bar absolute. The neutralization with aqueous alkali metal hydroxide solution in step d) produces a lighter organic phase and a heavier aqueous phase. The respective neutralizing agent is added preferably countercurrentwise or cocurrentwise in steps b) and d).

The mixture originating from step d) and taking the form of a two-phase mixture made up of aqueous phase and organic phase is separated in step e), by being decanted, for example. The aqueous phase from step e) may be combined with the aqueous phase originating from step c), and worked up jointly. Alternatively, the two aqueous phases may also be worked up separately from one another.

In accordance with one preferred embodiment of the invention, the aqueous phase removed in step e) is recycled to the neutralization in step d) and/or step b). This is advantageous if the aqueous phase still comprises unconsumed alkali metal hydroxide. This is generally the case if the second neutralizing stage is carried out with an excess of hydroxide, relative to the amount of acid not neutralized in the first neutralizing stage.

The aqueous phase obtained from step c), composed substantially of water, the ammonium salt, dissolved therein, of the acid catalyst employed, and also traces of the aniline and formaldehyde feedstocks, and also traces of the end product, MDA, is optionally combined with the aqueous phase originating from step e) and then is treated in step f) with at least one oxide and/or hydroxide of an alkaline earth metal. Preference is given to calcium oxide and/or calcium hydroxide, on account of their ready availability and the trouble-free handling and disposal of the resultant waste products. The calcium oxide/hydroxide may be employed in the form, for example, of milk of lime or slaked lime. In this case the ammonium salt is decomposed with formation of ammonia. This step of the process is known as a substep from the SOLVAY process for producing sodium carbonate. The ammonia is removed preferably by distillation or by stripping with steam or an inert gas.

The ammonia-rich gas phase is optionally concentrated and purified in further steps, such as drying by adsorption, distillation or extractive steam condensation; work-up by distillation is particularly preferred. In one preferred embodiment of the invention, the ammonia worked up is passed back to the neutralization in step b).

In one particular embodiment, the gas comprising steam and ammonia is passed over calcium oxide, also referred to as quicklime. In this procedure, the gas is firstly dried, and then the quicklime is converted into calcium hydroxide, so-called slaked lime, which in turn is supplied to the ammonium salt decomposition step f).

The low-ammonia-content liquid phase which is left after the removal of the ammonia may be disposed of as wastewater, optionally after further concentration or purification.

The organic phase obtained in step e), which predominantly is composed of MDA with residual amounts of water, ammonia, alkali metal hydroxide, and the feedstock products for preparing the MDA, is likewise worked up. This is done, for example, by washing one or more times with water and/or, preferably, by multiple distillation. Preferably, after step e), water and unreacted aniline are removed from the organic phase, by means of distillation, for example.

The MDA prepared by the process of the invention is typically reacted with phosgene to give MDI. Processes of this kind are general knowledge and have been widely described, as for example in Kunststoffhandbuch, volume 7, polyurethanes, Carl Hanser, Munich, Vienna, 3rd edition, 1993, pages 76 to 86, and also in a large number of patent applications, WO 99/40059 or WO 99/54289 being an example.

For this purpose, the MDA and optionally the phosgene are typically dissolved in an inert solvent and reacted. Solvents used are preferably inert organic solvents, more particularly aromatic solvents, such as toluene or halogenated aromatic compounds, such as monochlorobenzene.

Phase recovery may be carried out in typical reactors, examples being stirred tanks, stirred tank cascades, columns and/or tube reactors, at known temperatures of, for example, 50 to 150° C., preferably 70 to 120° C., more preferably 70 to 100° C., under a pressure of 0.5 to 10 bar.

The phosgenation may be carried out, for example, as a two-stage reaction in the presence of at least one inert organic solvent, in which case the first stage of the phosgenation is carried out in a static mixer and the second stage of the phosgenation in a residence apparatus.

The crude MDI prepared by the phosgenation can be purified by customary methods, such as distillation, for example. In a first purifying procedure, preferably, phosgene and optionally solvent can be removed preferably to a large extent, more preferably completely, from the reaction mixture from the phosgenation, i.e., from the crude MDI.

With preference, subsequently, desired monomeric MDI, as for example 2,2'-, 2,4'- and/or 4,4'-MDI, and/or mixtures comprising at least two of these isomers may be removed by means of a suitable method, preferably by distillation, at pressures for example of 2 to 50 mbar, preferably 2 to 20 mbar, and at temperatures of 150 to 250° C., preferably 180 to 230° C., and/or preferably by crystallization, an example being fractional crystallization.

In one particular embodiment of the process for preparing MDI, the bicyclic product can be removed from the crude MDA and reacted by gas phase phosgenation, as described by EP 570 799, for example, to give bicyclic MDI.

The MDI thus prepared may in particular be reacted with compounds having at least two active hydrogen atoms, to form polyurethanes.

The process of the invention allows cost-effective and operationally reliable work-up of MDA. There is no damage caused to the MDA. The ammonia used can be removed entirely from the reaction product. The circulation of the ammonia prevents product losses. The aqueous salt solutions produced can be disposed of with no problems. The MDI prepared by phosgenation from the MDA prepared by the process of the invention has improved color values.

The invention is elucidated in more detail in the examples below.

EXAMPLES

Example 1

Density Differences

The density differences were calculated for the organic phase and the aqueous phase after neutralization with aqueous sodium hydroxide solution and, respectively, with aqueous ammonia solution for the MDI reaction discharge from the reaction of aniline with formaldehyde in the presence of HCl, for different ratios of aniline to formaldehyde (NF) and of acid to aniline (AdA).

TABLE 1

| | Aqueous NaOH solution Density difference [kg/m$^3$] | | Aqueous NH$_3$ solution Density difference [kg/m$^3$] | |
| --- | --- | --- | --- | --- |
| Acid/ aniline [mol/mol] | Aniline/ formaldehyde: 1.8 mol/mol | Aniline/ formaldehyde: 2.4 mol/mol | Aniline/ formaldehyde: 1.8 mol/mol | Aniline/ formaldehyde: 2.4 mol/mol |
| 0.04 | 84.65 | 43 | 120 | 87 |
| 0.1 | 41 | −5 | 95 | 57 |
| 0.24 | −7.23 | −52 | 77 | 37 |

Density difference: density (organic phase)−density (aqueous phase)

A negative sign means that a phase inversion has taken place and that the aqueous phase is the heavier phase.

The density difference between the two phases alters markedly on neutralization with aqueous sodium hydroxide solution with increasing AdA ratio; with an A/F ratio of 2.4 mol/mol, there is a phase inversion between the AdA ratio of 0.05 and 0.1; with an A/F ratio of 1.8 mol/mol, the density difference between aqueous phase and organic phase becomes likewise smaller with increasing AdA ratio; the phase inversion takes place between an AdA ratio of 0.2 and 0.25.

In the case of the neutralization with aqueous NH$_3$ solution, the density difference always has the same sign, and hence there is no phase inversion, and the absolute values are also large enough to allow rapid phase separation.

Example 2

Preparation of MDA from aniline and formaldehyde with catalysis with HCl Formaldehyde and aniline (formaldehyde/aniline=2.4 mol/mol) were reacted in the presence of hydrochloric acid (HCl/aniline=0.07 mol/mol) at 50-90° C. and 1-1.5 bar.

Example 3 (Inventive)

Two-Stage Neutralization with NH$_3$ in the First Stage and with Aqueous NaOH in the Second Stage 2000 g of the reaction discharge as per example 1 were mixed with 200 g of 25% strength aqueous ammonia solution. The pH was 8.9. The aqueous phase was lighter than the organic phase. The two phases were separated. In the next step, the organic phase was admixed with about 77 g of sodium hydroxide solution (50% by weight). The pH of the mixture was 9.7. After phase separation had taken place, the phases were withdrawn separately from the laboratory apparatus. The aqueous upper phase withdrawn comprised about 6.24% by weight of chloride ions and had a fraction of about 3% by weight of sodium ions and a fraction of 3.1% by weight of ammonium ions.

Following phase separation, 956 g of the organic phase were washed in two stages with deionized water (phase ratio 0.28 kg/kg), and the aniline and residual water were distilled off at 125° C. and 18 mbar. The organic sample was subsequently phosgenated.

Example 4 (Comparative)

Single-Stage Neutralization with NH$_3$ 2 kg of the reaction discharge as per example 1 were mixed with about 200 g of 25% strength aqueous ammonia solution. The pH was 9.0. The aqueous phase was lighter than the organic phase. After phase separation had taken place, the two phases were withdrawn separately from the laboratory apparatus. The aqueous upper phase withdrawn comprised about 7% by weight of chloride ions and about 5% by weight of ammonium ions.

Following phase separation, 956 g of the organic phase were washed in two stages with deionized water (phase ratio 0.28 kg/kg), and the aniline and residual water were distilled off at 140° C. and 17 bar. The organic phase was subsequently phosgenated.

Example 5 (Comparative)

Single-Stage Neutralization with Aqueous NaOH 2.4 kg of the reaction discharge as per example 1 were admixed with 102 g of aqueous 50% strength sodium hydroxide solution. The pH was 10.8. The aqueous phase forms the lower phase. The phases were withdrawn separately from the laboratory apparatus. The aqueous lower phase withdrawn comprised about 8% by weight of chloride ions.

Following phase separation, 956 g of the organic phase were washed in two stages with deionized water (phase ratio about 0.28 kg/kg), and the aniline and residual water were distilled off at 140° C. and 17 mbar. The organic sample was subsequently phosgenated.

Example 6 (Inventive)

Neutralization with Gaseous NH$_3$, Aqueous NH$_3$ Solution, and Aqueous NaOH Solution 1400 g of the reaction discharge as per example 1 were admixed with 57 g of gaseous NH$_3$. The pH was 7.4. The organic phase was heavier than the aqueous phase. The organic phase removed (916 g) was admixed with 227 g of 25% strength aqueous $NH_3$ solution, producing a pH of 9.45 at 73° C. Continual gas evolution was observed during this procedure. After heating, the pH fell to 8.5. Subsequently, 3.7 g of aqueous NaOH solution (30%) were added. The pH thereafter was 9.5.

Example 7

Determination of Dihydroquinazoline Content

The dihydroquinazoline content was determined by gas-chromatographic analysis of the dissolved samples obtained from example 3. The solvent used was dimethylformamide (DMF) with 3 mg of tetramethyl-MDA per ml of DMF. Calibration took place with solutions of bicyclic dihydroquinazoline, of 4,4'-MDA, and of tricyclic MDA. A gas chromatograph (HP 5890) with flame ionization detector was used. The carrier gas used was $H_2$. The results of the analysis are set out in table 2. A value≤10 means that the content was below the detection limit.

TABLE 2

| Content [ppm] | MDA from ex. 3 (inventive) | MDA from ex. 4 (comparative) | MDA from ex. 5, (comparative) |
|---|---|---|---|
| Bicyclic dihydroquinazoline | ≤10 | ≤10 | ≤10 |
| Tricyclic dihydroquinazoline | ≤10 | ≤10 | 75 |
| Tetracyclic dihydroquinazoline | 11 | 19 | 90 |

The MDI prepared by the process of the invention has a lower overall content of dihydroquinazolines, which have an adverse effect on the color value.

Example 8

Determination of Color Values

The color values of the MDIs obtained from example 3 were determined iodometrically. A high value denotes severe coloration, a low value slight coloration.

The results are set out in table 3.

TABLE 3

| | Iodine color number |
|---|---|
| MDA from ex. 3 (inventive) | 23.2 |
| MDA from ex. 4 (comparative) | 23.3 |
| MDA from ex. 5 (comparative) | 28.8 |

The process of the invention leads to MDI having relatively low color values.

Example 9 (Inventive)

Recovery of Ammonia 1000 g of the aqueous phase obtained from the first neutralization of example 1 were admixed in a heated laboratory apparatus with 150 g of calcium hydroxide (slaked lime). The resultant, water-comprising gaseous ammonia was passed through a drying tower filled with calcium oxide, and thus dried. The dried ammonia could be used again for neutralization. Following complete degassing, the material which remained in the apparatus was an approximately 20% strength aqueous solution of calcium chloride, for disposal.

The invention claimed is:

1. A process for preparing diphenylmethanediamine and more highly condensed polyphenylenepolymethylenepolyamines, comprising:
   a) reacting aniline with formaldehyde in the presence of an acid,
   b) neutralizing a first part of the acid with ammonia or an aqueous ammonia solution, to obtain a first reaction mixture,
   c) separating the first reaction mixture into a first aqueous phase and a first organic phase,
   d) neutralizing a second part of the acid, present in the first organic phase, with an aqueous alkali metal hydroxide solution, to obtain a second reaction mixture,
   e) separating the second reaction mixture into a second aqueous phase and a second organic phase,
   f) treating the first aqueous phase or optionally a combination of the first and second aqueous phases with at least one oxide or hydroxide of an alkaline earth metal, to obtain a third reaction mixture, comprising ammonia, and
   g) removing the ammonia from the third reaction mixture.

2. The process of claim 1, wherein the acid comprises a mineral acid.

3. The process of claim 1, wherein the acid comprises hydrochloric acid.

4. The process of claim 1, comprising b) neutralizing the first part of the acid with an aqueous ammonia solution.

5. The process of claim 1, wherein the ammonia or the aqueous ammonia solution in b), and the aqueous alkali metal hydroxide solution in d), are added countercurrentwise or cocurrentwise.

6. The process of claim 1, further comprising recycling the second aqueous phase to the neutralizing d).

7. The process of claim 1, wherein the oxide or hydroxide of an alkaline earth metal in f) is calcium oxide or calcium hydroxide.

8. The process of claim 1, wherein the hydroxide of an alkaline earth metal in f) is calcium hydroxide.

9. The process of claim 1, further comprising recycling the ammonia from the third reaction mixture to the neutralizing b).

10. The process of claim 1, further comprising removing water and unreacted aniline from the second organic phase after e) or from the third reaction mixture after g).

11. The process of claim 1, further comprising purifying and working up the second organic phase to obtain purified diphenylmethanediamine and more highly condensed polyphenylenepolymethylenepolyamines.

12. The process of claim 11, further comprising reacting the purified diphenylmethanediamine with phosgene to obtain diphenylmethane diisocyanate.

13. The process of claim 1, wherein a molar ratio of aniline to formaldehyde in a) is in a range of 20 to 1.5.

14. The process of claim 1, wherein a molar ratio of aniline to formaldehyde in a) is in a range of 2.5 to 1.8.

15. The process of claim 1, wherein a molar ratio of the acid to aniline in a) is in a range of 0.04 to 0.5.

16. The process of claim 1, wherein a molar ratio of the acid to aniline in a) is in a range of 0.04 to 0.25.

17. The process of claim 1, wherein the reacting a) is performed at a pressure of 0.1 to 50 bar, absolute.

18. The process of claim 1, comprising b) neutralizing 60% of the acid with ammonia or an aqueous ammonia solution.

19. The process of claim 1, comprising b) neutralizing 90% of the acid with ammonia or an aqueous ammonia solution.

20. The process of claim 4, wherein the aqueous ammonia solution has an ammonia concentration of 14% to 60% by weight.

* * * * *